United States Patent [19]

Mays

[11] Patent Number: 4,904,186

[45] Date of Patent: Feb. 27, 1990

[54] ATTACHMENT FOR REMOVABLY SUPPORTING A DENTURE IN THE MOUTH OF THE USER

[76] Inventor: Ralph C. Mays, 6740 S. 69th East Ave., Tulsa, Okla. 74133

[21] Appl. No.: 221,212

[22] Filed: Jul. 19, 1988

Related U.S. Application Data

[63] Continuation-in-part of Ser. No. 90,456, Aug. 28, 1987, Pat. No. 4,784,608.

[51] Int. Cl.$^4$ ............................................. A61C 13/22
[52] U.S. Cl. ..................................... 433/172; 433/173
[58] Field of Search ................ 433/173, 176, 172, 170

[56] References Cited

U.S. PATENT DOCUMENTS 4,085,506  4/1978  Lew ..................................... 433/172

Primary Examiner—Robert Peshock
Attorney, Agent, or Firm—Head & Johnson

[57] ABSTRACT

An attachment for removably supporting a denture in the mouth of the user in which the user has at least two spaced apart dental posts implanted therein, the attachment including a first basic portion in the form of an anchor member semi-permanently attached to the anchor post and being curved to generally the shape of the alveolar ridge of the user and having a bar portion extending between the spaced apart dental posts, the anchor member having retention recesses at each end. The attachment's second basic portion is a denture member which conforms generally to the contour of the anchor member and which is engagable in proximity with the anchor member. The denture member is cast within a denture having simulated gum portions and teeth portions. The denture member has integrally formed projections which are removably insertable into the recesses in the anchor member, the axes of the projections and the axes of the recesses being inclined toward planes of the anchor member and the denture member. The denture member includes an arm pivotal between a locked and an unlocked position. The arm has a blade portion which extends underneath the anchor member so that the arm when in the locked position retains the denture within the mouth of the user. The bar portion is generally circular in cross-section and the projections and recesses are dimensioned to permit limited pivotal movement of the denture member relative to the anchor member when the denture is locked to the anchor member.

3 Claims, 4 Drawing Sheets

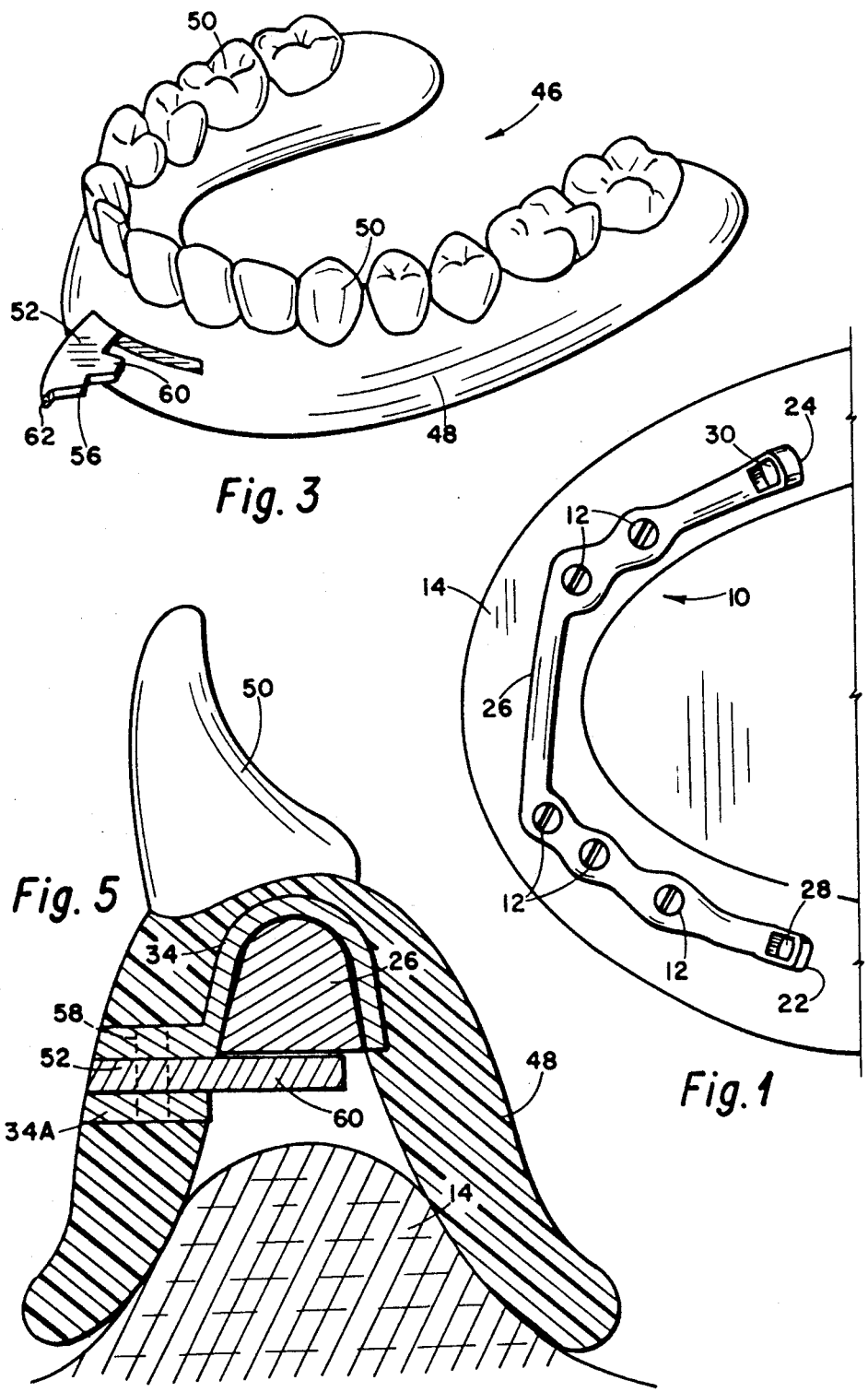

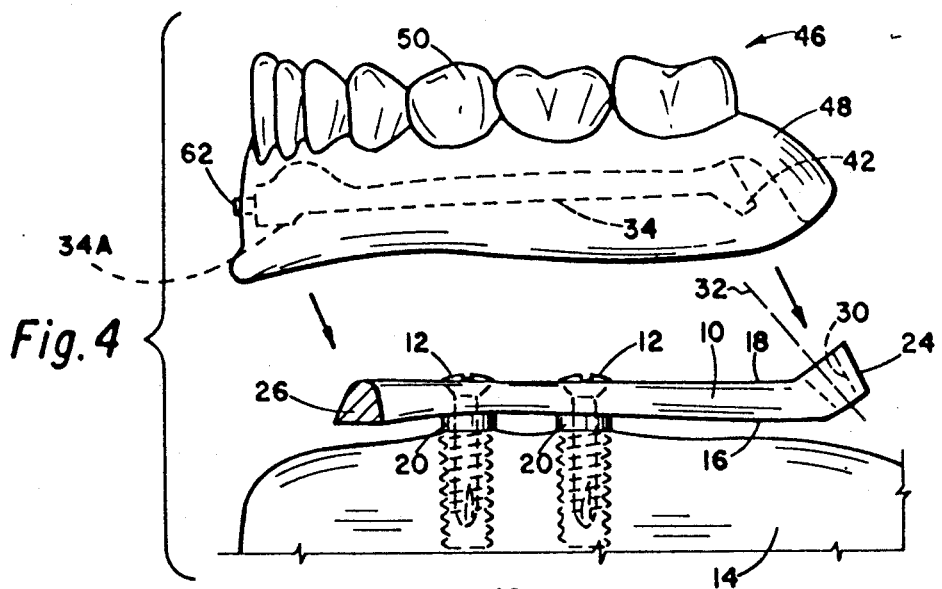
Fig. 4
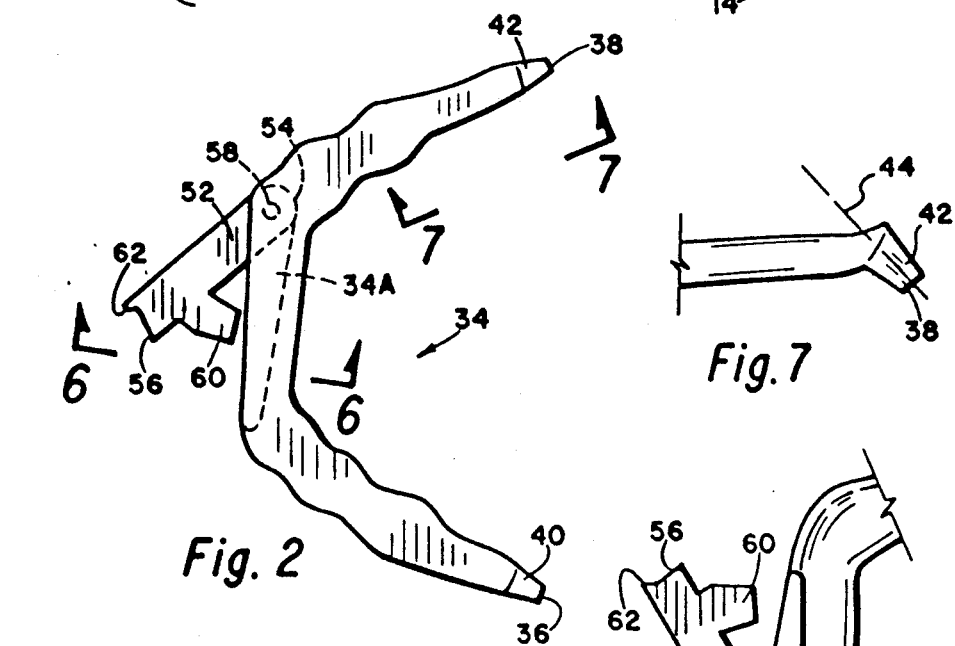
Fig. 2
Fig. 7
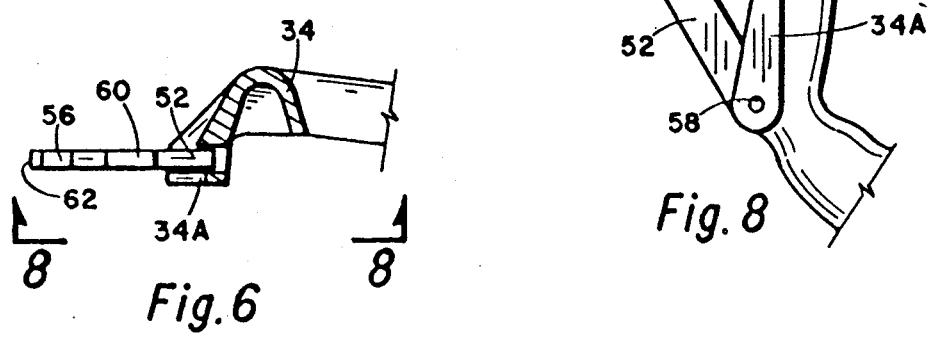
Fig. 6
Fig. 8

ATTACHMENT FOR REMOVABLY SUPPORTING A DENTURE IN THE MOUTH OF THE USER

CROSS-REFERENCEC

This is a continuation-in-part of application Ser. No. 090,456, filed August 28, 1987 and now U.S. Pat. No. 4,784,608 issued 11/15/88, Ralph C. Mays Applicant, entitled "ATTACHMENT FOR REMOVABLY SUPPORTING A DENTURE IN THE MOUTH OF THE USER".

SUMMARY OF THE INVENTION

The present invention is directed to an improved means of removably supporting a denture in the mouth of the user. When a person loses all their natural teeth, either upper or lower, but especially lower, the utilization of a denture is and has always been a problem. While dentures can be accurately fitted to the alveolar ridge of the user, it is difficult to retain a denture in position; that is, during normal chewing or talking, the denture has a tendency to ride up out of position on the alveolar ridge, causing speech difficulties, chewing difficulties, and general unsatisfactory use of a denture.

In recent years a practice has developed of permanently implanting dental posts in the bone structure of the mouth. These permanent metal posts are usually made of titanium which is more readily acceptable by the body's biological processes and which are locked into position by bone growth. By utilization of permanently installed posts in the mouth of the user, the possibility then exists for more readily securing a denture in place.

The present invention provides an improved attachment for removably supporting a denture in the mouth of the user using implants and in which the denture is secured, but in a way so that the denture is very conveniently removed and reinstalled in the user's mouth and wherein decreased stress is placed on the implants.

The attachment is formed by an anchor member which is fitted semi-permeably into the mouth of the user and anchored, such as by screws, to dental posts. In the usual arrangement the user will have at least two dental posts. The anchor member is fittable to the dental posts in a semi-permanent manner, such as by the use of screws. The anchor member is preferably a cast member formed by using an impression taken from the mouth of the users after the posts have been installed. The anchor member is typically generally U-shaped and in a common plane. The U-shaped anchor member has opposed ends and a middle portion. The middle portion is formed by a bar portion which extends between adjacent spaced-apart dental posts and is of generally circular configuration. The anchor member has a proximal surface adjacent to the user's alveolar ridge and an opposed distal surface.

A mating denture member is also cast to substantially conform to the distal surface of the anchor member. The denture member is generally of U-shaped configuration, conforming to the alveolar ridge shape of the user's mouth, and the U-shaped configuration is in a general plane. The denture member has opposed ends and a center portion. The anchor member has retention means at the opposed ends. The retention means are in the form of a recess at each end of the anchor member. Each recess is an opening which has an axis, and the axis of the opening is inclined relative to the plane of the anchor member and in the direction toward the anchor member center portion.

The denture member has retention means in the form of integral projections which are shaped and configured to be removably received within the anchor member recesses. The projections each have an axis of insertion which is at an angle relative to the plane of the U-shaped denture member. The recesses and projections are dimensioned to permit limited movement of the projections within the recesses.

The denture member is utilized by encapsulation in a denture having simulated gums and teeth. The denture member is then integral with the denture member. When the denture is inserted into the mouth of a user, the integral projection extending from the denture member at the ends thereof removably extend into the recesses in the anchor member so that the rear portion of the denture is retained in position but is permitted limited movement.

At or near the central portion of the denture member an arm is pivotally secured at one end. The arm has, adjacent the other end, a blade portion. The arm is pivoted between a locked and an unlocked position. When in the unlocked position the arm extends outwardly, away from the denture member center portion. When in the locked position the arm is moved pivotally toward the center portion so that the blade extends beneath the anchor member bar portion. Thus, when the denture having the denture member cast therein is positioned within the mouth of the user, the integral projections are loosely received in the recesses in the anchor member and the arm is moved to the locked position, the blade of which extends beneath the anchor member bar to thereby lock the denture into the mouth of the user in a manner which permits limited pivotation of the denture about the bar portion.

The outer end of the arm has a fingernail engaging portion. When the user desires to remove the denture, the arm is engaged by the fingernail of the user and is pivoted to the unlocked position, allowing the front of the denture to be lifted upwardly and thereby allowing the denture member integral projection to be removed from the anchor member recesses so that the entire denture is easily removed from the mouth of the user.

A better understanding of the invention will be had by reference to the following descriptions and claims, taken in conjunction with the attached drawings.

DESCRIPTIONS OF THE DRAWING

FIG. 1 is a top view of an anchor member portion of an attachment for removably supporting a denture in the mouth of the user, the anchor member being shown mounted on posts which have been permanently secured in the bone of the lower jaw of the user. FIG. 1 shows the alveolar ridge of the lower jaw with screws holding the anchor member to the permanently installed dental posts.

FIG. 2 is a top view of the other basic portion of the attachment, that is, a denture member which is cast of metal and configured to be encompassed within a denture. The denture member of FIG. 2 includes an arm, pivotable between a locked and an unlocked position and in FIG. 2 the arm is shown in the unlocked position.

FIG. 3 is an isometric view of a denture which has the denture member of FIG. 2 cast therein and showing the arm extending therefrom in the unlocked position.

FIG. 4 is an exploded view showing the denture of FIG. 1 having the denture member cast therein and showing a portion of the anchor member secured to dental posts permanently mounted into the jaw bone of the user and showing the direction which the denture is inserted onto the anchor member to securely lock the denture to the anchor member within the mouth of the user.

FIG. 5 is a cross-sectional view of a front portion of the mouth of the user showing the alveolar ridge and showing a denture positioned within the mouth of the user and in enlarged dimensions. The anchor member is shown in cross-section and the denture is also shown in cross-section. The denture includes simulated gums and teeth and with the arm in the locked position.

FIG. 6 is a cross-sectional view taken along the line 6—6 of FIG. 2 showing details of the construction of the denture member with the locking arm in the unlocked position.

FIG. 7 is a partial elevational view of an end portion of the denture member showing an integral projection which forms a retention means for retaining the denture in the mouth of the user.

FIG. 8 is a partial lower view of the center portion of the denture member taken along the line 8—8 of FIG. 6 showing the arm in the unlocked position.

Figures 9, 12:
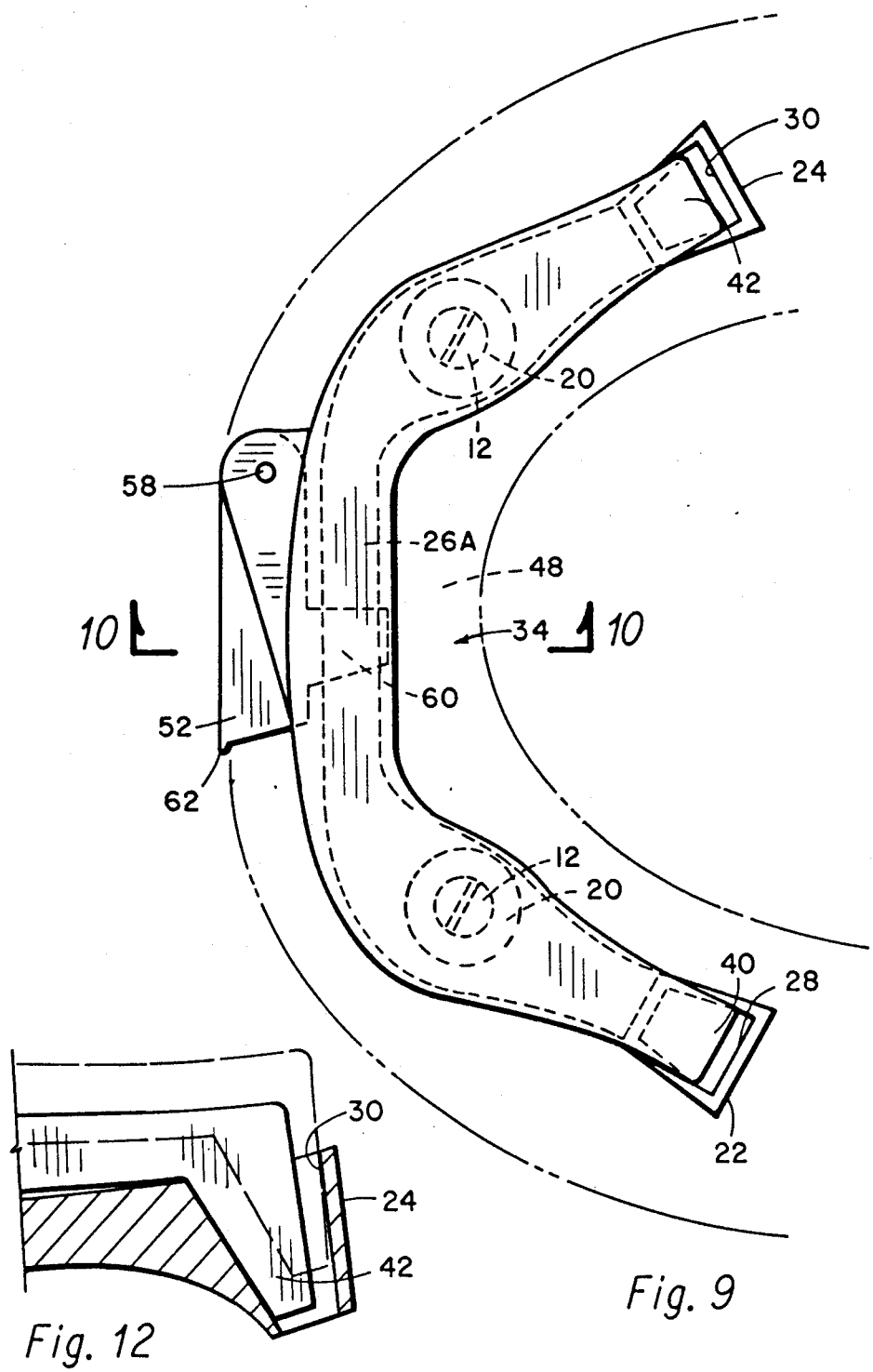

FIG. 9 is a top plan view of an embodiment of the anchor member supported within the mouth of the user and with the denture member secured thereto. The anchor member is supported by only two posts and the denture which normally is cast around the denture member is shown only in dotted outline to reveal the details of the anchor and denture members.

Figure 10:
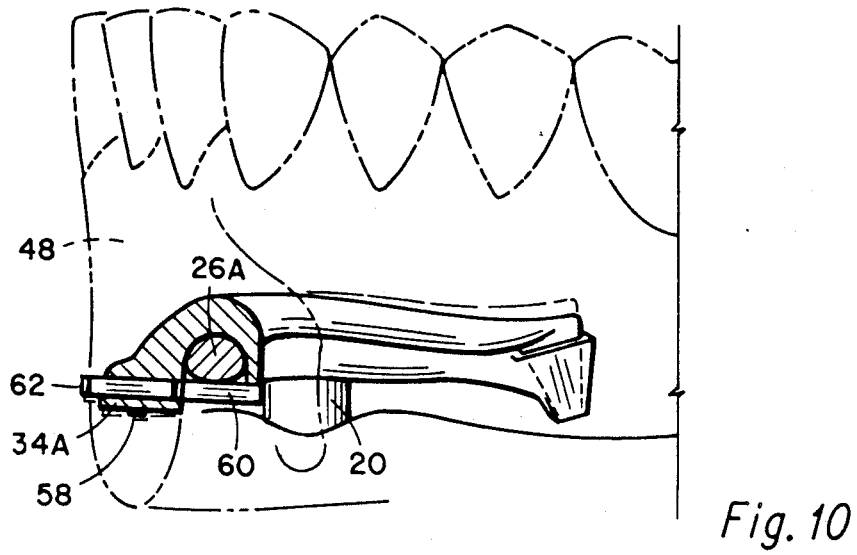

FIG. 10 is a cross-sectional view taken along the line 10—10 of FIG. 9 showing the denture member mounted in position on the anchor member and showing the denture which receives the denture member as a part thereof in dotted outline. FIG. 10 shows the denture as mounted in place in the mouth of the user.

Figure 11:
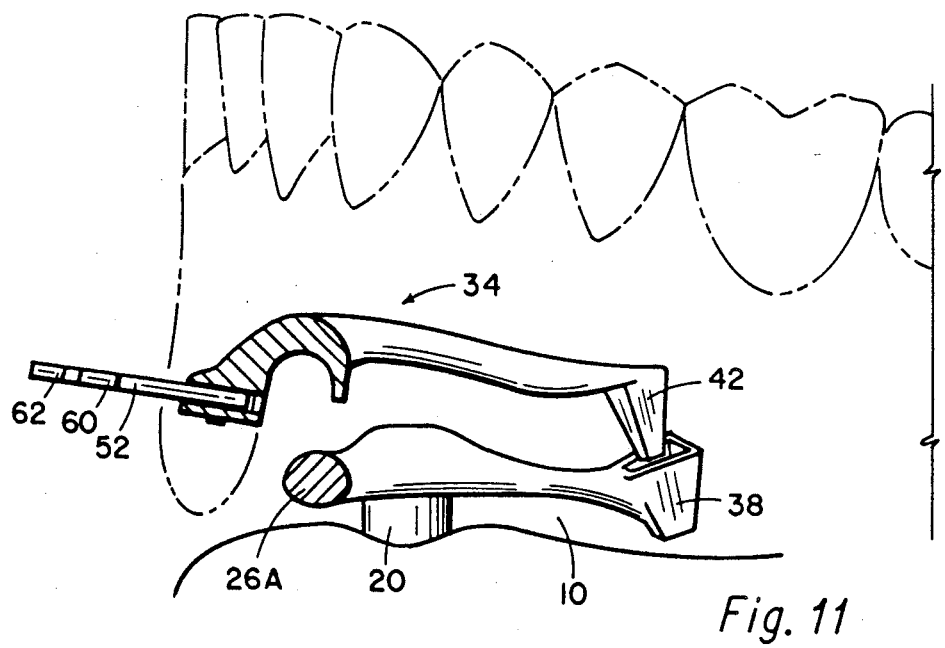

FIG. 11 is a cross-sectional view as in FIG. 10, but showing the denture member in the unlocked position and with the denture member in the attitude during insertion or removal of the denture from the mouth of the user.

FIG. 12 is an enlarged fragmentary view of one outer end of the anchor member showing the recess therein and showing the end portion of the denture member with the integral projection portion and showing in dotted outline the normal position of the denture member when the wearer has the denture member in his mouth, and wherein no pressure is being applied to the denture; that is, when no chewing action is taking place showing in solid outline the position when maximum chewing action is taking place, showing the flexibility of the retention system which permits at least a major portion of the stress of the denture to be transferred from the denture to the wearer's alveolar ridge rather than to the anchor member.

DESCRIPTION OF THE PREFERRED EMBODIMENT

The attachment of this invention for removably supporting a denture in the mouth of the user is formed of two basic portions. The first portion is an anchor member generally indicated by the numeral 10 and shown in plan view as would be employed for a lower denture in FIG. 1. The anchor member 10 is of the type to be attached to permanently installed dental posts in the user's mouth. Dental posts are inserted into the bone of the user's mouth such as by drilling into the bone and inserting or screwing the posts into position. Other means also are well known for securing posts in the mouth of the user. A dental post typically has a threaded recess therein and FIG. 1 shows the anchor member 10 secured to the dental posts by means of screws 12. The alveolar ridge 14 of the user's jaw is shown.

The anchor member 10 is formed by taking an impression of the mouth of the user after the dental posts are permanently installed. Using this impression the anchor member is cast of metal; and as shown in FIG. 4, has a proximal surface 16 which is adjacent to the top of the patient's alveolar ridge 14 and a distal surface 18 which is opposed to the proximal surface. FIG. 4 shows two of the dental posts 20 with screws 12 therein.

As shown in FIG. 1, the anchor member 10 is of generally U-shaped configuration conforming generally to the shape of the alveolar ridge 14 of the mouth of the user. The U-shaped configuration provides post ends 22 and 24, and a front or middle portion 26 which is intermediate the ends 22 and 24 and between spaced apart dental posts. The front portion forms a bar portion 26 extending across the front or near the front of the anchor member.

At or adjacent the anchor member ends 22 and 24 are retention means which preferably are in the form of recesses 28 and 30. As previously stated, the anchor member 10 is generally of a U-shaped configuration and is in a general plane. Each of the recesses 28 and 30 has an axis, the axis of recess 30 being indicated by the numeral 32 in FIG. 4. The axis of each recess is inclined at an angle relative to the plane of the anchor member. The angle is acute in the direction towards the front of the anchor member or toward the bar portion 26.

The other basic portion of the attachment is a denture member generally indicated by the numeral 34, a top view of which is seen in FIG. 2. The denture member is cast utilizing an impression. The denture member 34 fits in close, substantially contiguous contact with the distal surface 18 of the anchor member. Like the anchor members, the denture member is generally of U-shaped configuration and in a common plane. The denture member has ends 36 and 38 which are preferably in the form of integral projections 40 and 42. Each of the projections has an axis, the axis of projections 42 being illustrated by the dotted line 44 in FIG. 7. The axis of each projection 40 and 42 is inclined at an acute angle relative to the plane of the denture member 34, and preferably at the same or approximately the same angle as the angle of axis 32 of anchor member 10. The projections 40 and 42 are configured to be slidably inserted into the recesses 28 and 30 of the anchor member and when received in such recesses the denture member 34 cannot be dislodged by a direct upward pull on the denture member, but can only be removed by simultaneous forward and upward movement along the axis 32 of the recess.

The denture member 34 is encapsulated within a denture generally indicated by the numeral 46 in FIG. 3 and 4. The denture included simulated gum portions 48 and teeth 50. When encapsulated in a denture 48 the denture member 34 is exposed on the lower surface thereof to engage the anchor member 10 when the denture is in position. The denture member 34 is preferably of generally U-shaped cross-sectional configuration as shown in FIG. 5 at least in the forward or middle portion thereof with the balance of the denture member generally conforming to the distal surface of the anchor member.

Secured to the denture member 34 in the middle thereof, that is, between the opposed ends 36 and 38, is an arm 52 having a first end 54 and second end 56. The first end of the arm 52 is pivoted to the denture member 34 by means of a hinge pin 58. Integrally extending from the arm 52 is a blade portion 60. The second end 56 of the arm has a fingernail receiving portion 62.

To use the denture having the attachment member 34 secured therein in conjunction with an anchor member secured on dental posts within the mouth of the user, the denture is inserted onto the anchor member 10 as shown in FIG. 4. That is, the denture is inserted simultaneously downwardly and rearwardly, so that the projections 40 and 42 extend within the recess 28 and 30. The front portion of the denture 46 is then moved downwardly so that the denture member engages the upper surface of anchor member 10. During installation, the arm 52 must be in the open position as shown in FIGS. 2 and 3. When the denture is firmly downwardly in position, the arm is then moved to the closed position shown in FIGS. 4 and 5. In the closed position the arm is substantially fully retained within the gum portion 48 of the denture. The fingernail receiving portion 62 of the arm is slightly extended from the surface of the denture gum portion 48 so that when the user wishes to remove the denture his fingernail can be extended underneath the portion 62 enabling him to pivot the arm 52 to the unlocked position.

The denture member 34 includes an integral portion 34A which is below arm 52 and which supports the arm when in the closed position.

The attachment thus provides a highly effective means of anchoring dentures in the user's mouth when the user is having at least two dental posts installed.

Referring to FIGS. 9 through 12, an alternate embodiment of the invention is illustrated. FIGS. 9, 10 and 11 show the anchor member 10 as supported in the mouth of the user utilizing only two posts 20. The anchor member 10 is formed, as previously described, with a bar portion 26A extending between the posts 20 and with rearwardly extending portions terminating in recesses 30 which are inclined at an angle relative to the plane of the anchor member. Since the arrangement of FIGS. 9, 10 and 11 employ only two posts 20 the length of the opposed end portions of the anchor member are reduced since such end portions must cantilever away from posts 20.

Received on the anchor member 10 is a denture member 34 as has been previously described. The denture member has projections 40 and 42 at each end as previously described with the projections having an axis with an angle relative to the plane of the denture member extending at an acute angle. The denture member includes the locking arrangement for securing the denture member and denture affixed thereto, to the anchor member.

The embodiment of FIGS. 9 through 12 differs from that of the embodiments of FIGS. 1 through 8 that the anchor member and denture member are arranged so that a limited amount of pivotation is permitted. This is accomplished by providing the portion 26A of the anchor member with a cross-section which permits slight rotation of the denture member 34 relative to it; that is, the bar portion 26A is of generally circular or oval configuration rather than having a closely fitting configuration as shown in FIG. 5. This means that where the denture portion 34 locks to the anchor portion at the bar portion 26A, the denture member is free to pivot through a limited arch.

Another difference in the embodiment of FIGS. 9 through 12 is that the projections 42 and the recess openings 30 are dimensioned so that the projections can move through a limited arch within the recesses 30. This is illustrated in FIGS. 10 and 12. The projections retain the denture member and thereby the denture affixed thereto in the mouth of the user in the same manner as described with reference to FIGS. 1 through 8, but permit a slight amount of flexing of the denture.

In practicing the use of the attachment of this invention, the dentures are formed in such a way that the rearward portion of the dentures are supported by the user's alveolar ridge; that is, the portion of the mouth of the user from which teeth normally extend. The dentist using the attachment employs impressions for making the castings and mounting the finished denture to the denture member 34 in such a way that when the denture is in the mouth of the user, the projections 40 and 42 do not rest upon the bottom of the recess 28 and 30 nor does the rearward extending leg portion of the denture member rest upon the rearward extending leg portions of the anchor member, but there is some space therebetween. When the user applies force to the denture, particularly the rearward portion thereof such as in chewing, the force is applied from the denture to the user's alveolar ridge and not directly to the anchor member rearwardly extending portion. In this manner the trauma which would tend to pivot posts 20 is taken off the posts and the pressure is applied to the user's alveolar ridge which, by nature, is strong and resistive of force. Only when the user applies force to the front teeth of the denture which sits more or less directly over the posts, is force applied to the posts; however, this force is applied downwardly and does not generate a pivotation action which would occur when force is applied to the anchor member end portions.

While the relationship between the denture member and anchor member permit flexibility so that the chewing force is applied first to the alveolar ridge or gums of the user rather than as pivoting force against the posts which support the anchor member, nevertheless, the attachment prevents the denture from being displaced within the mouth of the user. The denture is removed and inserted in the same way that was described with reference to FIGS. 1 through 8 and is retained within the mouth of the user in the same way; that is, the dentures can not be removed without first removing the blade 60 which extends below the anchor member bar portion 26A to permit the projections 40 and 42 to be fully removed from the recesses 28 and 30.

Portions of the attachment may be supplied to dental laboratories in the form of plastic components which can be used making castings—the plastic components being melted away in the same manner that wax is melted away in a lost wax process. Other parts of the attachment may be supplied as formed of metal.

The claims and the specification describe the invention presented and the terms that are employed in the claims draw their meaning from the use of such terms in the specification. The same terms employed in the prior art may be broader in meaning than specifically employed herein. Whenever there is a question between the broader definition of such terms used in the prior art and the more specific use of the terms herein, the more specific meaning is meant.

While the invention has been described with a certain degree of particularity it is manifest that many changes may be made in the details of construction and the arrangement of components without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

What is claimed is:

1. An attachment for removably supporting a denture in the mouth of a user having at least two spaced apart dental posts installed in the users alveolar ridge, comprising:

an anchor member fitable semi-permanently into the mouth of the user for anchoring, such as by screws, to dental posts, the anchor member being curved to generally the shape of the alveolar ridge of the user and the anchor member having a bar portion extending between spaced apart dental posts, the anchor member having a proximal surface adjacent the user's alveolar ridge and an opposed distal surface;

a denture member which conforms generally to the anchor member and engagable in proximity with said anchor member distal surface, the denture member being castable into a denture having simulated gum portions and teeth portions, said anchor member having retention means and the denture member having retention means which removably interlocks with said anchor member retention means when a denture having said denture member formed thereon is in usable position within the mouth of the user, and the anchor member being of a curved form within a general plane and said denture member being a generally correspondingly curved form within a general plane, said planes being generally parallel to each other when said denture member is formed in a denture and the denture is in position within the mouth of a user, (and) said anchor member retention means being in the form of spaced apart recesses each having an axis inclined at generally the same acute angle relative to said anchor member plane and said denture member retention means being in the form of integrally extending projections removably receivable within said anchor member recesses, each projection having an axis inclined at generally the same acute angle relative to said denture member plane, said recesses and projections being dimensioned to permit limited movement of said denture member relative to said anchor member; and locking means attached to said denture member releasably engagable with said anchor member bar portion and moveable between a locked and an unlocked position, whereby when said locking means is in the unlocked position a denture having said denture member may be inserted into or removed from the mouth of a user, said anchor member bar portion and said locking means configured to permit limited pivotal movement therebetween, said denture member being pivotable about said bar member within limits established by said recesses and projections when said denture member is locked to said anchor member.

2. An attachment member according to claim 1 wherein said locking means is in the form of an arm having a first and a second end, and having the first end pivoted to said denture member whereby the arm is pivotal between a locked and an unlocked position, the arm having adjacent the second end a blade portion, and having at the second end fingernail engaging means whereby the second end may be engaged by the fingernail of the user to pivot the arm to the unlocked position, the blade portion engaging said anchor member bar portion when said arm is pivoted to the locked position.

3. An attachment member according to claim 3 wherein said anchor member and said denture member are each of a generally U-shaped configuration corresponding to the general shape of the alveolar ridge of the user and each having opposed ends and a center portion intermediate the ends and wherein said anchor member and said denture member retention means are at the opposed ends of the respective members and wherein said anchor member bar portion is at said anchor member center portion and wherein said locking means is at said denture member center portion, and wherein said bar portion is substantially circular in cross-section in the area receiving said locking member blade portion.

* * * * *